United States Patent [19] [11] 4,393,512
Wang [45] Jul. 12, 1983

[54] HYPER-FILTER-FLUORESCER SPECTROMETER FOR X-RAYS ABOVE 120 KEV

[75] Inventor: Ching L. Wang, Livermore, Calif.

[73] Assignee: The United States of America as represented by the United States Department of Energy, Washington, D.C.

[21] Appl. No.: 281,141

[22] Filed: Jul. 7, 1981

[51] Int. Cl.³ .............................................. G01N 23/22
[52] U.S. Cl. ..................................... 378/156; 378/44; 378/145; 378/157
[58] Field of Search .................. 378/145, 44, 157, 156

[56] References Cited

U.S. PATENT DOCUMENTS

| 3,176,130 | 3/1965 | Brinkerhoff | 378/145 |
|---|---|---|---|
| 3,456,108 | 7/1969 | Pichoir . | |
| 3,581,087 | 5/1971 | Brinkerhoff . | |
| 3,854,049 | 12/1974 | Mistretta . | |
| 3,919,548 | 11/1975 | Porter . | |
| 3,920,999 | 11/1975 | Drexler . | |
| 3,944,822 | 3/1976 | Dzubay . | |
| 4,189,645 | 2/1980 | Chaney . | |

OTHER PUBLICATIONS

"Filtered Detector Arrays for Single Pulse Photon Measurements Above 100 keV", Tirsell, Livermore Laboratories, UCRL 80314, 11/09/77.

"Filter Fluorescer Experiment on the Argus Laser", Kornblum, Livermore Laboratories, UCRL 81471, 10/10/78.

"A Ten Channel Filter-Fluorescer Spectrometer", Pruett, Livermore Laboratories, UCRL 81477, 10/31/78.

Primary Examiner—Craig E. Church
Attorney, Agent, or Firm—Miguel A. Valdez; Clifton E. Clouse, Jr.; Richard G. Besha

[57] ABSTRACT

An apparatus utilizing filter-fluorescer combinations is provided to measure short bursts of high fluence x-rays above 120 keV energy, where there are no practical absorption edges available for conventional filter-fluorescer techniques. The absorption edge of the prefilter is chosen to be less than that of the fluorescer, i.e., $E_{PRF} < E_F$, contrary to the prior art technique $E_{PRF} > E_F$. In this way, the response function is virtually zero between $E_{PRF}$ and $E_F$ and well defined and enhanced in an energy band of less than 1000 keV above the 120 keV energy.

9 Claims, 13 Drawing Figures

HYPER-FILTER-FLUORESCER SPECTROMETER FOR X-RAYS ABOVE 120 KEV

It is a result of Contract No. W-7405-ENG-48 between the U.S. Department of Energy and the University of California for the operation of the Lawrence Livermore National Laboratory.

BACKGROUND OF THE INVENTION

The invention relates generally to filter-fluorescer combinations for measuring short bursts of high-fluence x-rays, and more particularly, it relates to measuring such bursts in energies above 120 keV, where no practical material absorption edges exist for conventional filter-fluorescer techniques.

To determine the fluence in different energy bands below 120 keV emitted by a high-fluence x-ray source, the prior art uses a pre-filter, a fluorescer, and a post-filter, all with properly selected absorption edges. The responses of this combination are shown in graphs a-d of FIG. 1. With the pre-filter absorption edge $E_{PRF}$ determining the upperbound of the energy band of interest, and the fluorescer $E_F$ and post-filter $E_{POF}$ absorption edges coinciding with the lower bound of the energy band, the result is a joint response function with a sharply defined high transmission in the energy band $E_F < E < E_{PRF}$, a sharp transmission fall-off for energies $E < E_F$ and markedly attenuated transmission for energies $E < E_{PRF}$. As used herein, an absorption edge is the energy corresponding to an absorption discontinuity in the intensity of an x-ray absorption spectrum, which gives the appearance of a sharp edge in such a spectrum. Also, an energy band is a zone between two different energies in the x-ray spectrum. Combinations to achieve a sharply defined type of high transmission are described in the papers "Filter Fluorescer Experiment on the Argus Laser" (preprint UCRL-81471) published Oct. 10, 1978, by H. N. Kornblum et al; and "A Ten Channel Filter-Fluorescer Spectrometer" (preprint UCRL-81477) published Oct. 31, 1978, by B. L. Pruett et al.

In a paper entitled "Filtered Detector Arrays for Single Pulsed Photon Measurements Above 100 keV" (preprint UCRL-80314) published Nov. 9, 1977, by K. G. Tirsell and H. C. Catron, the authors show that the spectrometer range may be extended to x-ray energies around 250 keV by replacing the filter-fluorescer combination with a simple filter-detector combination; i.e., a combination including only filters and detectors. The reason for this replacement in prior art is that above 120 keV there are no practical absorption edges available for conventional filter-fluorescer techniques. As shown in FIG. 2, the result with the simple filter-detector combination is a response function having an energy transmission band of 200 to 5000 keV width. This bandwidth, however, is too broad for energy discrimination purposes. Furthermore, one or more undesirable windows (such as W1 and W2 of FIG. 2) appear at lower bands corresponding to lower absorption edges of the filter material. These windows introduce a large error in the detector signal when the spectrum being measured is a rapidly decreasing function of the x-ray energy. This limitation is particularly troublesome when measuring x-rays from a gold source, since the windows occur in the region where the gold K-lines are present.

These problems related to the filter-fluorescer technique, establish the need for a well-defined response function when measuring high-fluence x-ray energies above 120 keV.

It is, accordingly, a general object of the invention to measure high-fluence x-rays above 120 keV energy, where there are no practical absorption edges available, for conventional filter-fluorescer techniques.

Another object of the invention is to improve the channel response function in measuring high-fluence x-rays above 120 keV by narrowing the energy transmission band to a width suitable for energy discrimination purposes.

Another object is to eliminate undesirable response windows in measuring high-fluence x-rays above 120 keV and to ensure that these windows vanish in the region where the gold K-lines appear.

Other objects, advantages, and novel features of the invention will be apparent to those of ordinary skill in the art upon examination of the following detailed description of a preferred embodiment of the invention and the accompanying drawings.

SUMMARY OF THE INVENTION

In brief, the invention relates to a method and apparatus in which a new filter-fluorescer combination to measure short bursts of high fluence x-rays above 120 keV is utilized. By predetermining the associated absorption edges of this combination so that the absorption edge of the fluorescer is equal to the post-filter absorption edge and more than the pre-filter absorption edge, the joint response function in the band range $E_{PRF} < E < E_F$ is virtually 0 and the response for bands greater than $E_F$ is found to be well defined and enhanced.

One important difference between the prior art and the present invention is that the absorption edges in the prior art are preselected so that $E_{PRF} < E_F = E_{POF}$ while in the invention $E_{PRF} < E_F = E_{POF}$.

DESCRIPTION OF THE PREFERRED EMBODIMENT

Figure 1A:
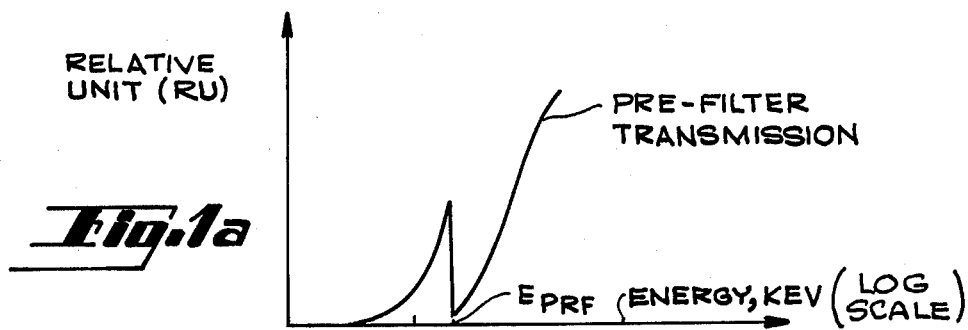
FIG. 1 is a graph showing the pre-filter and post-filter transmissions, the fluorescer cross-section (cross section is a quantity which is proportional to the probability of x-ray interaction in the fluorescer and is measured as an area), and the joint response of a conventional filter-fluorescer spectrometer.
Figure 1B:
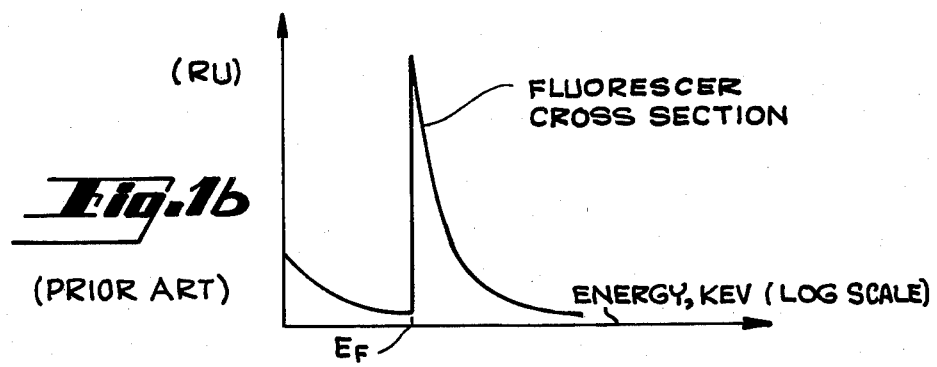
Figure 1C:
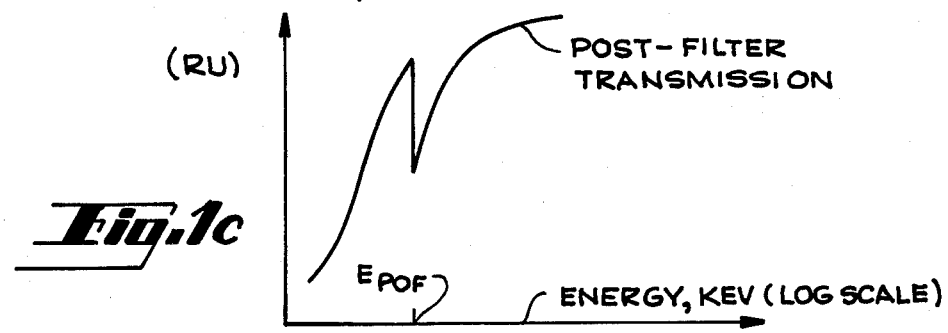
Figure 1D:
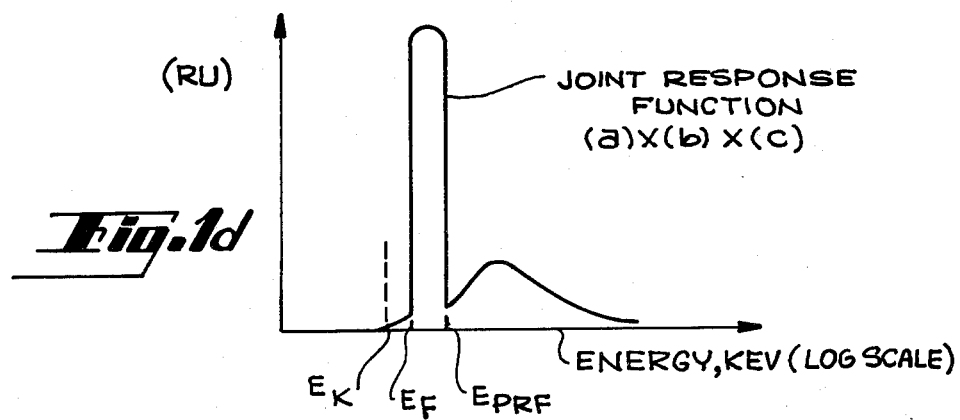
Figure 2:
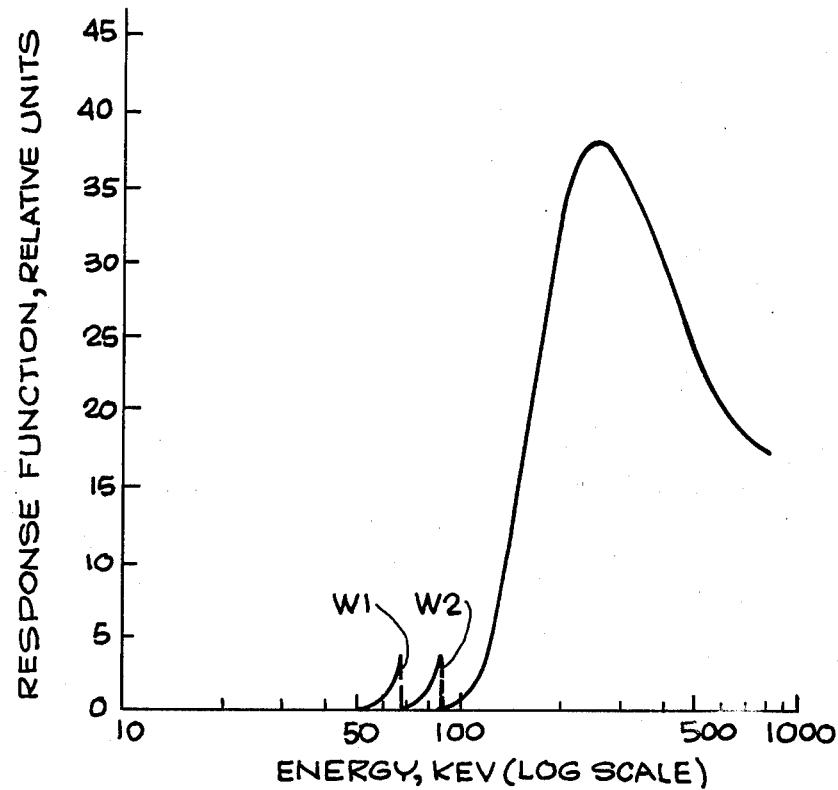
FIG. 2 is a graph showing the response function of a simple filter-detector spectrometer channel.

Turning now to the drawings, FIG. 1 shows the response of a conventional spectrometer with a filter-fluorescer combination having an absorption edge $E_{POF}$ less than absorption edge $E_{PRF}$ and equal to absorption edge $E_F$. This conventional combination results in a sharply defined high transmission in the energy band $E_F < E < E_{PRF}$ below 120 keV. FIG. 2 shows a conventional single-filter spectrometer channel where the high transmission occurs above 120 keV, in an energy band of 200 to 5,000 keV, which is too broad for energy discrimination purposes. This is a prior art attempt to measure short bursts of high-fluence x-rays above 120 keV.

Figure 3:
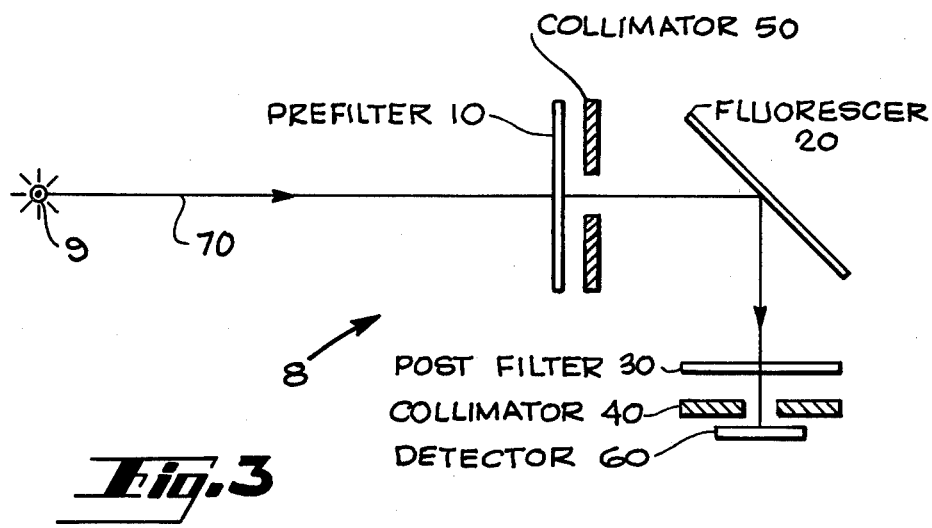
FIG. 3 is a schematic diagram of a filter-fluorescer spectrometer.

Reference will now be made in detail to the present preferred embodiment of the invention. Referring to FIG. 3, a filter-fluorescer spectrometer combination is used for measuring high-fluence x-rays above 120 keV. Still referring to FIG. 3, the filter-fluorescer spectrometer 8 consists of a pre-filter 10 having a predetermined absorption edge $E_{PRF}$, a post-filter 30 having a predetermined absorption edge $E_{POF}$ which is more than $E_{PRF}$, a slab of fluorescer material 20 having a predetermined absorption edge $E_F$ which is equal to $E_{POF}$, a detector 60 and two collimators, 40 and 50. The pre-filter 10, post-filter 30 and fluorescer 20 are made of selected materials in order to obtain the required absorption edges. The pre-filter 10 transmits the high x-ray flux emitted from an x-ray source toward the fluorescer 20. The collimator 50 receives this x-ray flux from the pre-filter 10 directing it as a parallel beam toward the fluorescer 20. The fluorescer 20 is oriented so as to receive the x-ray flux coming from the collimater 50 and re-emit it as K-fluorescence lines toward the post-filter 30. The post-filter 30 will improve the signal-to-noise ratio by transmitting preferentially the K-fluorescence lines $E_k$ of the x-ray flux while absorbing unwanted x-rays such as higher shell fluorescence or background x-rays. The collimator 40 will direct the emerging x-ray flux, as a parallel beam, from the post-filter 30 toward the detector 60.

Figure 4A:
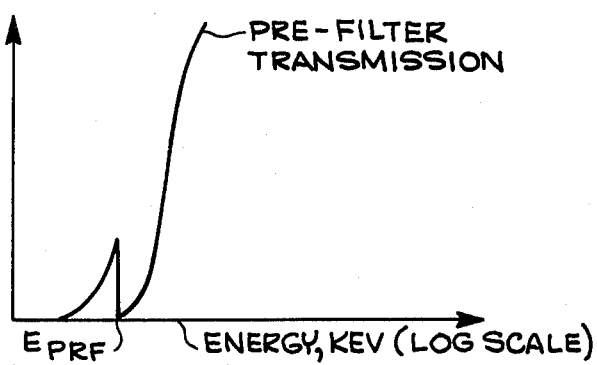
FIG. 4 is a graph showing the pre-filter and post-filter transmissions, the fluorescer cross-section and the joint response of a hyper filter-fluorescer spectrometer.
Figure 4B:
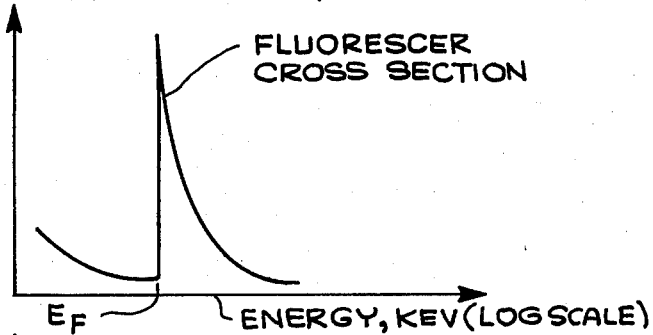
Figure 4C:
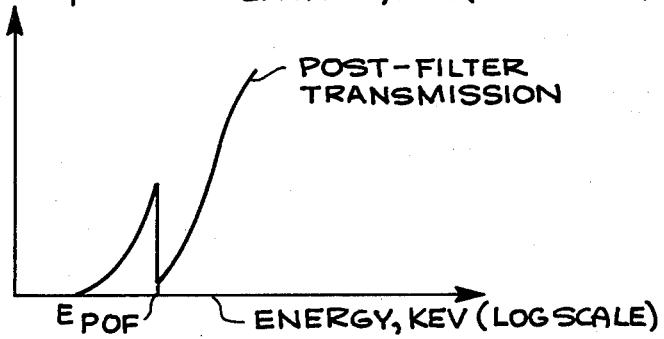
Figure 4D:
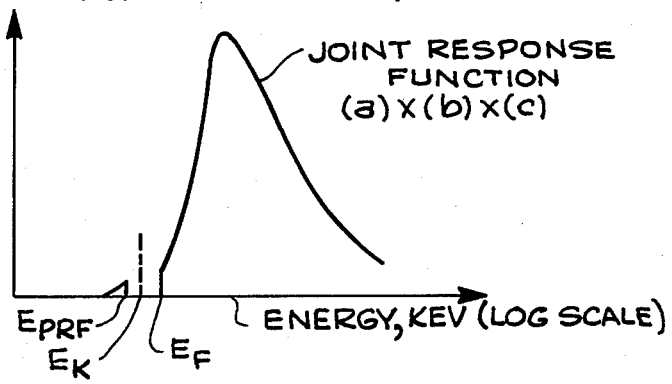

By selecting the thickness and material of the pre-filter 10, post-filter 30 and fluorescer 20, the band range $E_{PRF}<E<E_F$ can be adjusted to ensure that the response function vanishes in the region where the gold K-lines appear when measuring x-rays from a gold x-ray source. This is accomplished by imposing $E_{PRF}<$ gold K-lines $<E_F$ to assure that no gold K-lines between $E_{PRF}$ and $E_F$ energies will be detected by the x-ray detector 60, thereby avoiding a large error in the detector signal. Only the K-fluorescence lines $E_K$ will appear in the band range $E_{PRF}<E<E_F$, as shown in FIG. 4(d).

FIG. 4(a,b,c) illustrates the pre-filter, fluorescer and post-filter responses of the above embodiment with absorption edges chosen as $E_{PRF}<E_F=E_{POF}$. This combination results in the joint response function shown in FIG. 4(d), where the response in the energy band $E_{PRF}<E<E_F$ is virtually 0, because there is a joint maximum absorption of that combination in this band. Also no undesirable windows, such as in FIG. 2, will appear in this energy band. In energies greater than $E_F$, the response function is sharper and the energy transmission band is narrower than the response function in FIG. 2.

Figure 5:
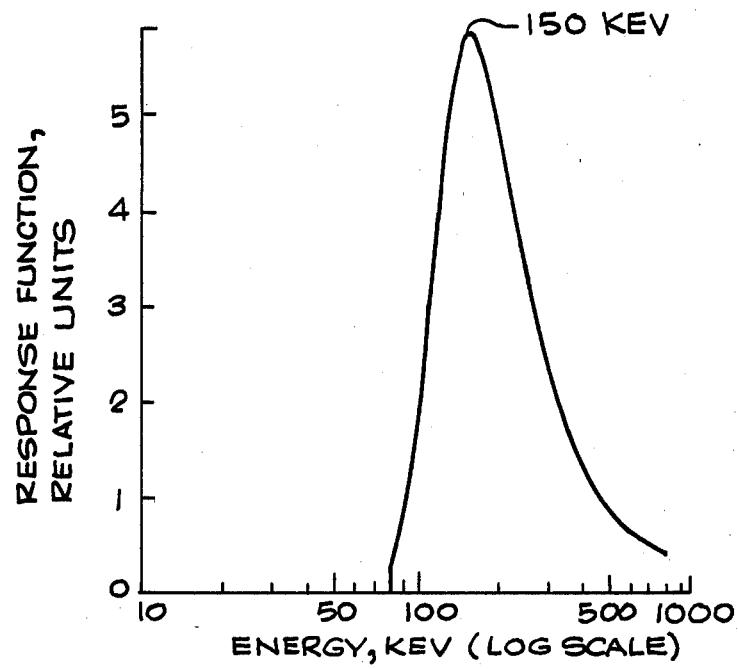
FIGS. 5 and 6 are additional graphs showing the response function of two hyper filter-fluorescer spectrometer channels.

An example of the above-explained embodiment is shown in FIG. 5, which illustrates a channel response function of the filter-fluorescer spectrometer 8 shown in FIG. 3 using a 48-microns thickness pre-filter of dysprosium, 29-microns thickness fluorescer of gold and a 9-microns thickness post-filter of gold. This response function rises from almost 0 at 80 keV to a maximum at 150 keV, and falls to 0 again near 1000 keV.

Figure 6:
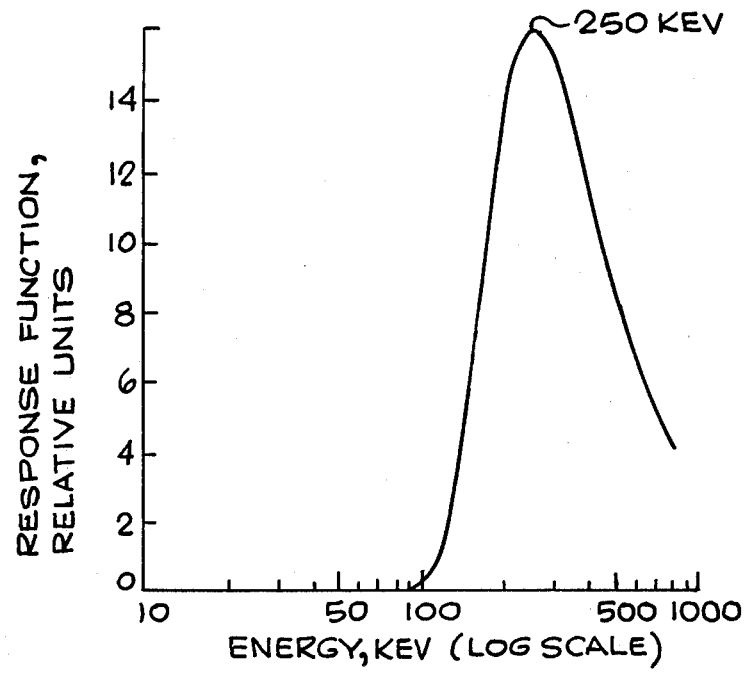

Another example of the same embodiment is shown in FIG. 6, which illustrates a channel response function of the filter-fluorescer spectrometer 8 shown in FIG. 3 using a 53-microns thickness pre-filter of hafnium, 10-microns thickness fluorescer of lead, and a 21-microns thickness post-filter of ytterbium. This response function rises from 0 at 90 keV to a maximum at 250 keV and falls to 0 again at an energy somewhat greater than 1000 keV.

The foregoing description of a preferred embodiment of the invention and examples have been presented for purposes of illustration and description. Further embodiments or combinations of those described herein will be apparent to those skilled in the art; and many modifications and variations are possible in the light of the above teaching. For example, by properly choosing the pre-filter, fluorescer, post-filter material and thickness, the peak position of the response function may be adjusted for any channel.

This modification is illustrated in the following table of physical parameters for four spectrometer channels with different peak positions at 150, 200, 250 and 300 keV:

| Spectrometer Energy (keV) | ELEMENTS PARAMETERS OF FOUR HYPER FILTER-FLUORESCER SPECTROMETER CHANNELS | | | | | | Detector NaI (TI) (mm) |
|---|---|---|---|---|---|---|---|
| | Pre-Filter | | Fluorescer | | Post-Filter | | |
| | M | T (mm) | M | T (mm) | M | T (mm) | |
| 150 | Dy | 1.27 | Au | .0762 | Au | .254 | 3 |
| 200 | Hf | 1.37 | Pb | .27 | Pb | .381 | 3 |
| 250 | Hf | 1.27 | Pb | .254 | Yb | .559 | 3 |
| 300 | Au | 2.03 | Pb | .0508 | Pb | .508 | 3 |

M = Material
T = Thickness

Figure 7:
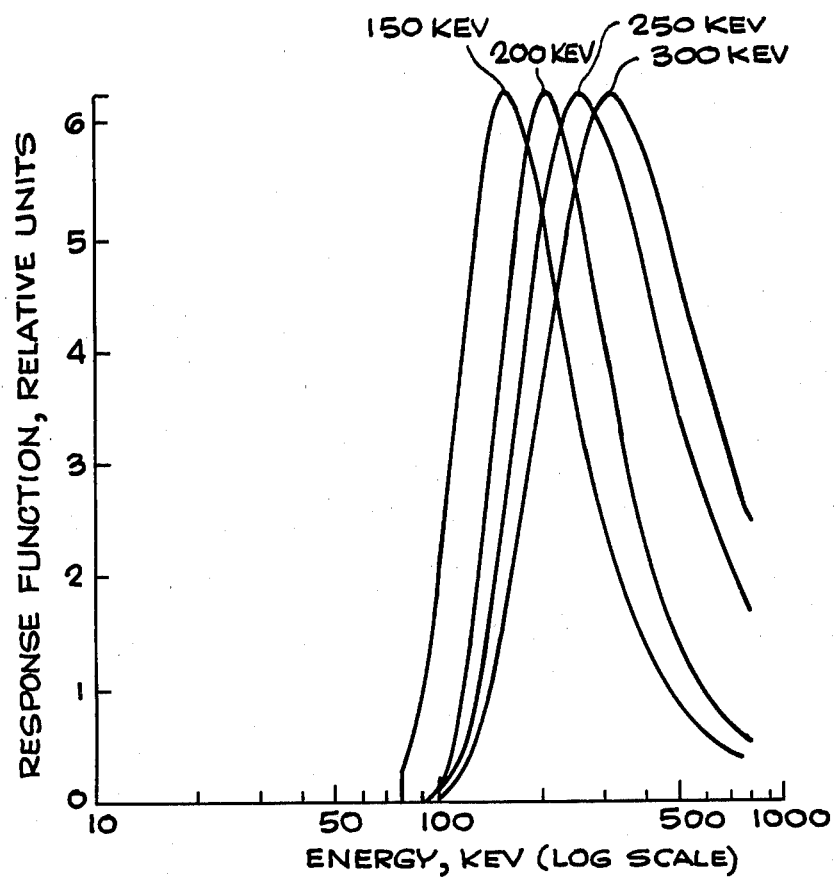
FIG. 7 is a graph showing the response function of four hyper filter-fluorescer spectrometer channels with different peak positions af 150, 200, 250 and 300 keV.

FIG. 7 illustrates the resulting response functions for those four spectrometer channels.

It is intended that the scope of the invention be defined by the claims appended hereto.

What is claimed is:

1. In a spectrometer system to provide measurements of x-rays, wherein these x-rays emitted from a source are transmitted through a pre-filter, directed by a first collimator to a fluorescer, re-emitted from the fluorescer as K-fluorescence lines toward a post-filter and directed again by a second collimator to an x-ray detector, the improvement which comprises:

said pre-filter for transmitting x-rays, having a predetermined absorption edge;
said post-filter for transmitting x-rays to said detector, having a predetermined absorption edge which is more than the absorption edge of said pre-filter; and
said fluorescer for emitting K-fluorescence lines toward said post-filter, having a predetermined absorption edge substantially equal to the absorption edge of said post-filter.

2. The improvement of claim 1, wherein the absorption edges of said pre-filter, post-filter and fluorescer are predetermined to eliminate undesirable transmission in the energy band between said fluorescer and pre-filter absorption edges.

3. The improvement of claim 2, wherein the adjustment of said energy band by preselecting the thickness and material of said pre-filter, post-filter and fluorescer, eliminates the detection by said detector of the gold K-lines emitted when measuring x-rays from a gold target.

4. The improvement of claim 1, wherein the thickness and material of said pre-filter, post-filter and fluorescer are preselected to adjust the response function peak position of said spectrometer system.

5. The improvement of claim 1, wherein said absorption edges are predetermined to provide x-ray measurements in an energy band of less than 1000 keV above 120 keV energy.

6. The improvement of claim 1, wherein said post-filter thickness and material is preselected to improve the signal-to-noise ratio by transmitting the K-fluorescence lines of said x-rays and absorbing the fluorescence or background x-rays.

7. A method for measuring x-rays above 120 keV energy, in a spectrometer system comprising a pre-filter, two collimators, a fluorescer, a post-filter and a detector, including the steps of:
   transmitting said x-rays by said pre-filter having a predetermined absorption edge;
   transmitting said x-rays to said detector by said post-filter having a predetermined absorption edge which is more than the absorption edge of said pre-filter;
   re-emitting said x-rays as K-fluorescence lines toward said post-filter, by a fluorescer having a predetermined absorption edge equal to the absorption edge of said post-filter.

8. The method of claim 7, which further comprises the steps of:
   adjusting the response function peak position of said spectrometer system for a desired energy band by preselecting the thickness and material of said post-filter, pre-filter and fluorescer;
   adjusting said energy band in less than 1000 keV for x-ray measurements above 120 keV, by preselecting said absorption edges.

9. The method of claim 7, which further comprises the step of:
   adjusting the energy band between said fluorescer and pre-filter absorption edges of said spectrometer system in order to eliminate the detection by said detector of the gold K-lines when measuring x-rays from a gold source.

* * * * *